United States Patent
Xing et al.

(10) Patent No.: US 12,077,496 B2
(45) Date of Patent: Sep. 3, 2024

(54) METHOD FOR SEPARATING C8 AROMATIC HYDROCARBON ISOMER MIXTURE

(71) Applicant: ZHEJIANG UNIVERSITY, Hangzhou (CN)

(72) Inventors: Huabin Xing, Hangzhou (CN); Xili Cui, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 166 days.

(21) Appl. No.: 17/911,126

(22) PCT Filed: Mar. 26, 2021

(86) PCT No.: PCT/CN2021/083120
§ 371 (c)(1),
(2) Date: Sep. 12, 2022

(87) PCT Pub. No.: WO2021/197211
PCT Pub. Date: Oct. 7, 2021

(65) Prior Publication Data
US 2023/0141078 A1 May 11, 2023

(30) Foreign Application Priority Data
Apr. 2, 2020 (CN) .................. 202010253913.X (51) Int. Cl.
*C07C 7/12* (2006.01)
*B01D 53/04* (2006.01)
*B01J 31/18* (2006.01)

(52) U.S. Cl.
CPC ............ *C07C 7/12* (2013.01); *B01D 53/0423* (2013.01); *B01J 31/181* (2013.01); *B01D 2253/204* (2013.01)

(58) Field of Classification Search
None
See application file for complete search history.

(56) References Cited

U.S. PATENT DOCUMENTS

| 515,913 | A | 3/1894 | Larsson et al. |
| 2,985,589 | A | 5/1961 | Broughton et al. |

(Continued)

OTHER PUBLICATIONS

Wang, Shi-Qiang et al., "Highly selective, high-capacity separation of o-xylene from C8 aromatics by a switching adsorbent layered material", Angewandte Chemie, Int'l Ed. vol. 58, No. 20, Feb. 21, 2019, pp. 6630-6634.

(Continued)

*Primary Examiner* — Ali Z Fadhel
(74) *Attorney, Agent, or Firm* — Jiwen Chen; Joywin IP Law PLLC (57) ABSTRACT

The present invention discloses a method of separating C8 aromatic hydrocarbon isomers. The anion-pillared metal-organic framework materials with a pore diameter of 5-10 Å is used as adsorbents to achieve selective adsorption and separation of C8 aromatic hydrocarbon isomers by contacting the C8 aromatic hydrocarbon isomers with the adsorbents; the anion-pillared microporous materials are porous materials formed by metal ion M, inorganic anion A and organic ligand L through coordination bonds, with the general formula of $[MAL_2]_n$, where $n>4$ and n is an integer; the descried "metal ion M" is $Fe^{2+}$, $Co^{2+}$, $Ni^{2+}$, $Cu^{2+}$; the descried "inorganic anion A" is $SiF_6^{2-}$, $NbOF_5^{2-}$, $TaF_7^{2-}$, $ZrF_6^{2-}$, $TiF_6^{2-}$, $GeF_6^{2-}$, $SO_3CF_3^-$, $NbF_6^-$; the descried "organic ligand L" is selected from any of the following:

(Continued)

-continued

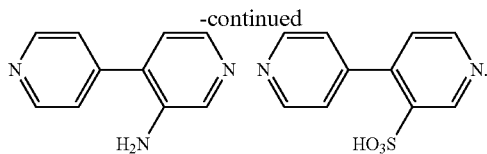

10 Claims, 5 Drawing Sheets (56) References Cited

U.S. PATENT DOCUMENTS

| | | | |
|---|---|---|---|
| 3,040,777 A | 6/1962 | Carson et al. | |
| 3,214,247 A | 10/1965 | Broughton | |
| 3,422,848 A | 1/1969 | Liebman et al. | |
| 3,686,342 A | 8/1972 | Neuzil | |
| 3,707,550 A | 12/1972 | Stine et al. | |
| 3,997,620 A | 12/1976 | Neuzil | |
| 8,262,775 B2 * | 9/2012 | Farha | C07C 51/412 502/4 |
| 8,704,031 B2 * | 4/2014 | Kulprathipanja | C07C 7/12 585/828 |
| 9,504,986 B2 * | 11/2016 | Zaworotko | B01J 20/226 |
| 9,611,218 B2 * | 4/2017 | Van Der Boom | C08G 83/00 |
| 10,118,877 B2 * | 11/2018 | Long | C07C 7/12 |
| 2016/0361702 A1 * | 12/2016 | Cohen | B01J 20/262 |
| 2017/0189890 A1 | 7/2017 | Holcroft et al. | |
| 2017/0246584 A1 * | 8/2017 | Eddaoudi | B01D 53/02 |
| 2018/0215684 A1 * | 8/2018 | Rungta | C07C 5/2732 |
| 2022/0258145 A1 * | 8/2022 | Ma | H01M 8/04216 |

OTHER PUBLICATIONS

S. Pillai, Renjith et al., "Computational prediction of promising pyrazine and bipyridine analogues of a fluorinated MOF platform . . . " Physical Chemistry Chemical Physics., vol. 21, No. 29, Jun. 27, 2019, pp. 16127-16136.

Guillerm, Vincent et al., "Continuous One-Step Synthesis of Porous M-XF6-Based Metal-Organic and Hydrogen-Bonded Frameworks." Chemistry—A European jurnal., vol. 23, No. 28, Mar. 30, 2017, pp. 6829-6835.

* cited by examiner

METHOD FOR SEPARATING C8 AROMATIC HYDROCARBON ISOMER MIXTURE

This is a U.S. national stage application of PCT Application No. PCT/CN2021/083120 under 35 U.S.C. 371, filed Mar. 26, 2021 in Chinese, claiming priority of Chinese Application No. 202010253913.X, filed Apr. 2, 2020, all of which are hereby incorporated by reference.

FIELD OF THE INVENTION

The present invention relates to chemical engineering area, and in particular to a method of separation of C8 aromatic hydrocarbon isomers.

BACKGROUND TECHNOLOGY

P-xylene (PX) is a basic organic chemical raw material, has been widely used in the synthesis of terephthalic acid (PTA), which is the monomer of polyesters, especially polyethylene terephthalate (PET). As the global demand of polyester soars, demand of PX is growing rapidly. Recently, China has become a major consumer and importer of PX, and the annual consumption of PX reached 23.85 million tons in 2017 with a consumption growth rate of 11.67%, and the imports accounted for 60%, mainly from Japan and South Korea.

Mixed C8-aromatics are typically derived from steam cracking, catalytic reforming and toluene disproportionation, which mainly comprises xylene isomers (PX, m-xylene (MX), o-xylene (OX)) and ethylbenzene (EB). Separation of mixed C8-aromatics is the main approach for preparing PX. However, due to their similar physical and chemical properties, closed density and boiling points, for example, the difference of boiling points between PX (138.35° C.) and MX (139.0° C.) is merely 0.35° C., it is challenging to separate them by conventional distillation. To date, the technologies for separating PX usually involve simulated moving bed (SMB) separation, crystallization, chemical complexation extraction, adsorption-crystallization integrated separation, etc. Among them, the SMB technology plays a dominant role in PX purification, which was first reported in the U.S. Pat. No. 2,985,589A. Subsequently, patents such as U.S. Pat. Nos. 3,040,777A, 3,214,247A, and 3,422,848A disclosed the equipments and control systems in SMB technology, the main techniques of which are UOP's Parex and MXSorbex. Based on SMB technology, PX can be separated and purified through adsorption, elution and distillation eluent processes using molecular sieve as the adsorbent. Specially, toluene is used as eluent in Parex process. Moreover, U.S. Pat. Nos. 3,686,342A, 3,707,550A, 3,997,620A, 5,159,131A and other patents disclosed the adsorptive separation of PX using barium or barium potassium type X or Y faujasite zeolites as the adsorbents.

Simulated moving bed (SMB) technology is efficient for separation, whereas it suffers from some problems, such as large instrument investment, easy loss and small handling capacity. Apart from that, the low separation selectivity, small capacity and intensive energy consumption for desorption of the adsorbents result in extremely high consumption in energy and solvent for PX separation. Therefore, it is important and essential to develop novel highly selective adsorbents and efficient PX separation and purification technology.

Recently, metal-organic frameworks (MOFs) with specific pore structures and functional sites have been found the availability of selective adsorption and separation for C8-aromatics. U.S. Pat. No. 8,704,031B2 reported two PX-selective adsorbents, Al-MIL-53 and Zn-MOF-5, and used SMB technology to separate xylene mixtures with p-diethylbenzene and toluene as eluents. Furthermore, patent US20180215684A1 reported MIL-125-NH$_2$, MIL-140b, MOF-48 adsorbents that selectively and preferentially adsorbed PX, and patent US20170189890A1 reported the separation of C8 aromatics by cyclodextrin-like MOF (CD-MOF) adsorbents. However, with the development of the technology for the synthesis of xylene from toluene disproportionation, the yield of PX has reached up to 80%-95%, and the above PX-selective MOFs inevitably go through several adsorption-desorption cycles to obtain high-purity PX products, resulting in an increment of energy consumption. Hence, designing OX-selective and MX-selective adsorbents can obtain high-purity PX with reduced energy cost. The patent U.S. Ser. No. 10/118,877B2 reported a class of MOF-74 adsorbents that preferably adsorbed MX and OX, with high adsorption capacity but low separation selectivity. In general, current MOFs suffer from poor molecular recognition and low adsorption capacity in C8-aromatics separation, undoubtedly, there is an urgent demand to develop novel separation materials and methods.

SUMMARY OF THE INVENTION

In view of the shortcomings in this field, the present invention provides a method of separating C8 aromatic hydrocarbon isomers using the anion-pillared metal-organic framework materials as adsorbents to achieve C8 aromatic hydrocarbon isomers selective adsorption and separation.

The present invention provides a method for separating C8 aromatic hydrocarbon isomers, wherein the anion-pillared metal-organic framework materials are the adsorbents, which can contact with C8 aromatic hydrocarbon isomers, thus achieving selective adsorption and separation of the mixture of C8 aromatic hydrocarbon isomers.

In such embodiments, the anion-pillared microporous materials are porous materials formed by metal ion M, inorganic anion A and organic ligand L through coordination bonds, with the general formula of $[MAL_2]_n$, where n>4 and n is an integer;

The descried "metal ion M" is $Fe^{2+}$, $Co^{2+}$, $Ni^{2+}$, $Cu^{2+}$.

The descried "inorganic anion A" is $SiF_6^{2-}$, $NbOF_5^{2-}$, $TaF_7^{2-}$, $ZrF_6^{2-}$, $TiF_6^{2-}$, $GeF_6^{2-}$, $SO_3CF_3^-$, $NbF_6^-$.

The descried "organic ligand L" is selected from any of the following:

The anion-pillared microporous materials used in this invention is porous crystalline materials with high surface area and high pore volume ratio, prepared from metal ions, inorganic anions and organic ligands. In addition, the pore structures and inorganic anion functional sites of these materials can response to different xylene isomers, and then carry out structural adjustments to recognize the difference in shape of C8 aromatic hydrocarbons, thereby obtaining very high separation selectivity. For example, it is found in this invention that the adsorption capacity of p-xylene on the anion-pillared microporous material, academically named ZU-61 (The metal ion is $Ni^{2+}$, the inorganic anion is $NbOF_5^{2-}$, and the organic ligand is 4,4'-bipyridine) is as high as 3.4 mmol/g, and the separation selectivity of m-xylene/p-xylene is as high as 2.9, showing really good application prospects in the separation of C8 aromatic hydrocarbons.

The structure of the anion-pillared microporous materials described here prepared by the organic ligands, metal ions and inorganic anions is as follows:

The descried pore size of the anion-pillared microporous materials is 5-10 Å.

The descried anion-pillared microporous materials can be prepared by using existing technologies, such as solid-phase grinding method, slow interface diffusion method, solvothermal method, room temperature co-precipitation method, and the like.

Preferably, the term "metal ion M" is $Ni^{2+}$ or $Cu^{2+}$, the descried "inorganic anion A" is $NbOF_5^{2-}$, $SiF_6^{2-}$ or $TiF_6^{2-}$, and the descried "organic ligand L" is 4,4'-bipyridine.

Preferably, the descried mixture of C8 aromatic hydrocarbon isomers is gaseous and/or liquid, which contains at least two of p-xylene, m-xylene, o-xylene and ethylbenzene.

The descried anion-pillared microporous materials have pore structure with size of 5-10 Å, and the pores contain highly ordered inorganic anions, which can realize the high-efficiency separation of the mixture of o-xylene, m-xylene, p-xylene, and ethylbenzene.

Preferably, the descried "organic ligand L" of anion-pillared microporous materials is 4,4'-bipyridine, which can form these materials with 5-10 Å pore size by coordinating with metal ion M and inorganic anion A. The order of adsorption strength for the mixture of C8 aromatic isomers is: o-xylene, m-xylene, ethylbenzene and p-xylene. As mentioned above, the adsorption of PX is weak, so the separation and purification of PX is realized, and the purity of p-xylene is more than 99%.

The separation method demonstrated in this present invention is suitable for the separation of isomer mixture of C8 aromatic hydrocarbons with different content and composition. In addition, the mass percentage concentration of p-xylene, m-xylene, o-xylene and ethylbenzene in the mixture can be 1-99%, and the C8 aromatic isomers can be a mixture of two or more of the above aromatics, and the mixture state would be gaseous or liquid. The anion-pillared microporous materials have good stability, so the mixture of C8 aromatic hydrocarbon isomers can contain other impurity components, such as one or more of water, methane, nitrogen, carbon dioxide, hydrogen, benzene, C7, C9 components, etc.

The shape of the anion-pillared microporous materials disclosed here is unlimited, and could be amorphous particles or spherical or cylindrical particles after molding.

In the separation method of this present invention, the contact mode of the adsorbent and the C8 aromatic hydrocarbon isomers can be any one of fixed-bed adsorption and simulated moving bed adsorption. Moreover, the C8 aromatic isomers can be in liquid or gas form, and the adsorption operation can be temperature swing adsorption or pressure swing adsorption.

Preferably, the adsorption temperature is 20-250° C. And it is further optimized to be 40-160° C.

Preferably, the pressure for the adsorption would be 0.1-5 bar. And it is further optimized to be 0.2-2 bar.

Preferably, the contact mode is fixed-bed adsorption, specifically including the following steps:

1) The mixture of C8 aromatic hydrocarbon isomers was introduced into a fixed-bed adsorption column. The strongly adsorbed C8 components were adsorbed on the adsorbent, and the specific C8 components that were not adsorbed or had low adsorption capacity were first penetrated to obtain the specific C8 components;

2) After the breakthrough and adsorption process of specific C8 components were completed, the strongly adsorbed C8 components were desorbed from the adsorbent by means of decompression desorption, heating desorption, desorber desorption or inert gas purging to obtain the strongly adsorbed C8 components.

Preferably, the desorption temperature is 20-250° C. And it is further optimized to be 50-150° C.

The separation method of this invention obtains p-xylene, m-xylene, o-xylene and ethylbenzene in the mass percentage, with the highest purity of more than 99%, and the maximum of 99.999%.

The present invention also provides the application of the anion-pillared microporous materials in the selective adsorption and separation of C8 aromatic isomers. Preferably, the descried mixture of C8 aromatic isomers is gaseous and/or liquid, which contains at least two of p-xylene, m-xylene, o-xylene and ethylbenzene.

Compared with the prior art, the main advantages of the present invention include:

1) The present invention provides a method for the first time to separate C8 aromatic hydrocarbon isomers by using anion-pillared microporous materials with pore size of 5-8 Å as adsorbents. Compared with traditional adsorbents, the anion-pillared metal microporous materials have the advantages of adjustable pore structure, large pore volume, adjustable interactions with adsorbate molecules, etc., and their special pore structure can realize the shape selective and efficient separation of C8 aromatics. For example, the anion-pillared metal microporous material named ZU-61 described here has the separation selectivity of m-xylene/p-xylene as high as 2.9, achieving selective separation of C8 aromatic isomers in different size and shape.

2) The described anion-pillared microporous materials in this present invention have relatively high adsorption capacity for C8 aromatic hydrocarbon isomers due to the relatively high pore volume rate and high-density functional sites. For example, it was found in this invention the adsorption capacity of the anion-pillared microporous material academically named ZU-61 for meta-xylene is as high as 3.4 mmol/g, which saves the amount of the adsorbent.

3) The order of the adsorption strength of the anion-pillared microporous materials demonstrated in this present invention on the C8 aromatic mixture is: o-xylene, m-xylene, ethylbenzene, and p-xylene. For PX adsorption is weak, the one-step single-column method can obtain high-purity p-xylene (purity higher than 99.9%, mass percentage), which is better than the simulated moving bed process based on conventional molecular sieves.

4) This method can obtain high-purity p-xylene, m-xylene, o-xylene, and ethylbenzene products according to industrial needs, up to 99.999% purity (mass percentage);

5) The anion-pillared microporous materials of the present invention have the advantages of simple synthesis method, easy amplification and preparation, and low cost. In addition, the adsorbents are recyclable easily, reusable, low energy consumption and low cost, which are suitable for industrialization.

DETAILED DESCRIPTION OF THE EMBODIMENTS

The present invention would be further explained below in conjunction with the drawings and specific embodiments. And these embodiments are provided for illustration only, not for the purpose of limiting the invention as defined by the appended claims and their equivalents. For unrecited specific conditions of the operation methods in the following examples, it is usually in accordance to the normal conditions, or the conditions recommended by the manufacturer.

Example 1

An ethylene glycol solution of 4,4'-bipyridylacetylene was mixed with an aqueous solution of 0.27 g $Cu(BF_4)_2 \cdot xH_2O$ and 0.20 g $(NH_4)_2SiF_6$ under stirring and then heated at 60-70° C. for 1-12 hours. The obtained SIFSIX-1-Cu was further filtered and then washed with methanol. After vacuum activation at 25-80° C. for 2-6 hours, the activated SIFSIX-1-Cu material obtained.

Figure 1:
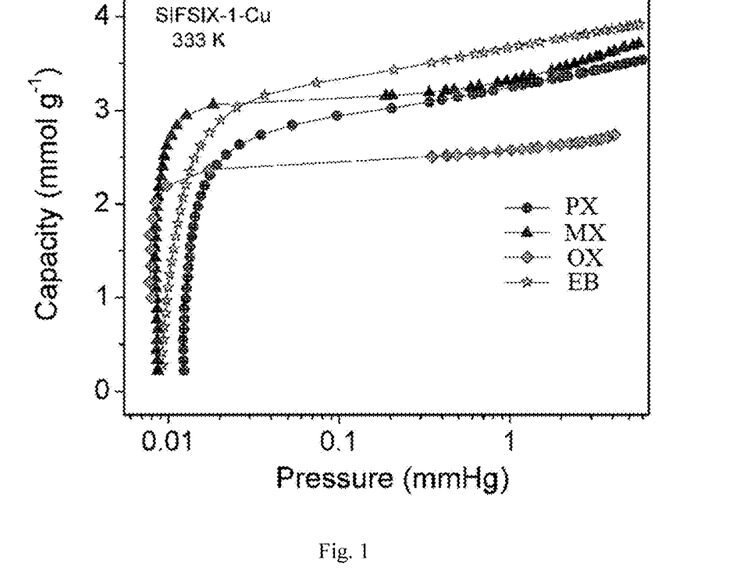
FIG. 1 shows the adsorption isotherms of p-xylene, m-xylene, o-xylene and ethylbenzene at 60° C. (333K) for the anion-pillared microporous material obtained in the example 1.

The adsorption isotherms of p-xylene isomers and ethylbenzene at 60° C. (333K) for SIFSIX-1-Cu are shown in FIG. 1.

Example 2

Figure 2:
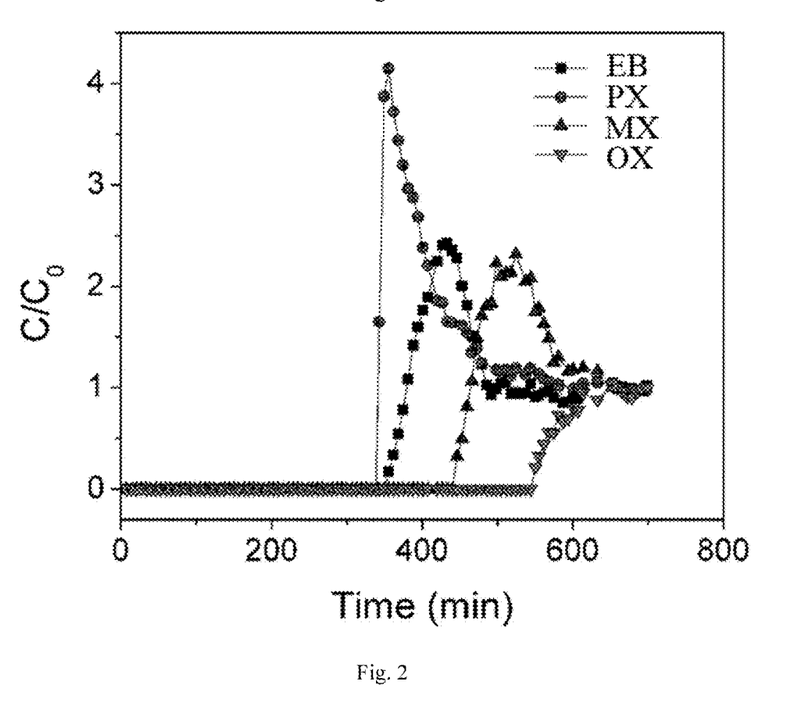
FIG. 2 shows the breakthrough curves obtained in the example 2.

The SIFSIX-1-Cu prepared in example 1 was loaded into a 50 mm long column, then the p-xylene, m-xylene, o-xylene and ethylbenzene (1/1/1/1, mass ratio) mixture obtained through nitrogen bubbling was introduced into the column at 20-40 mL/min with an operating temperature of 60° C. The breakthrough curve is shown in FIG. 2, and high-purity p-xylene can be obtained from the effluent gas.

Example 3

The ternary p-xylene, m-xylene and o-xylene (1/1/1, mass ratio) gas mixture obtained through nitrogen bubbling was introduced into the column of example 2 at 20-40 mL/min with an operating temperature of 60° C. High-purity p-xylene (over 99.9%, mass percentage) can be obtained from the effluent gas.

Example 4

An ethylene glycol solution of 4,4'-bipyridylacetylene was mixed with an aqueous solution of $NiNbOF_5$ under stirring and then heated at 60-70° C. for 1-12 hours. The obtained ZU-61 was further filtered and then washed with methanol. After vacuum activation at 25-150° C. for 2-8 hours, the activated ZU-61 material obtained.

Figure 3:
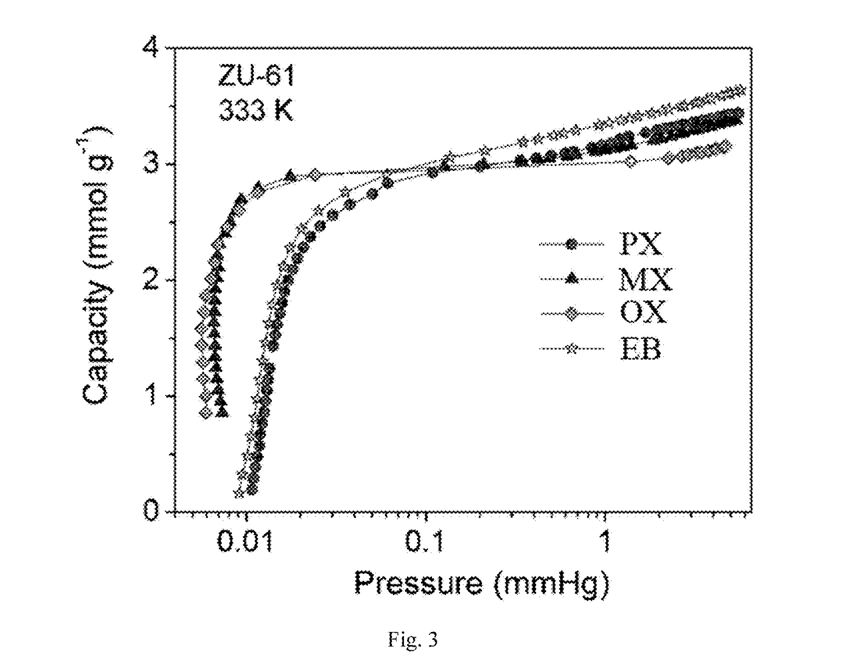
FIG. 3 shows the adsorption isotherms of p-xylene, m-xylene, o-xylene and ethylbenzene at 60° C. (333K) for the anion-pillared microporous material obtained in the example 4.

The adsorption isotherms of p-xylene isomers and ethylbenzene at 60° C. for ZU-61 material are shown in FIG. 3.

Example 5

Figure 4:
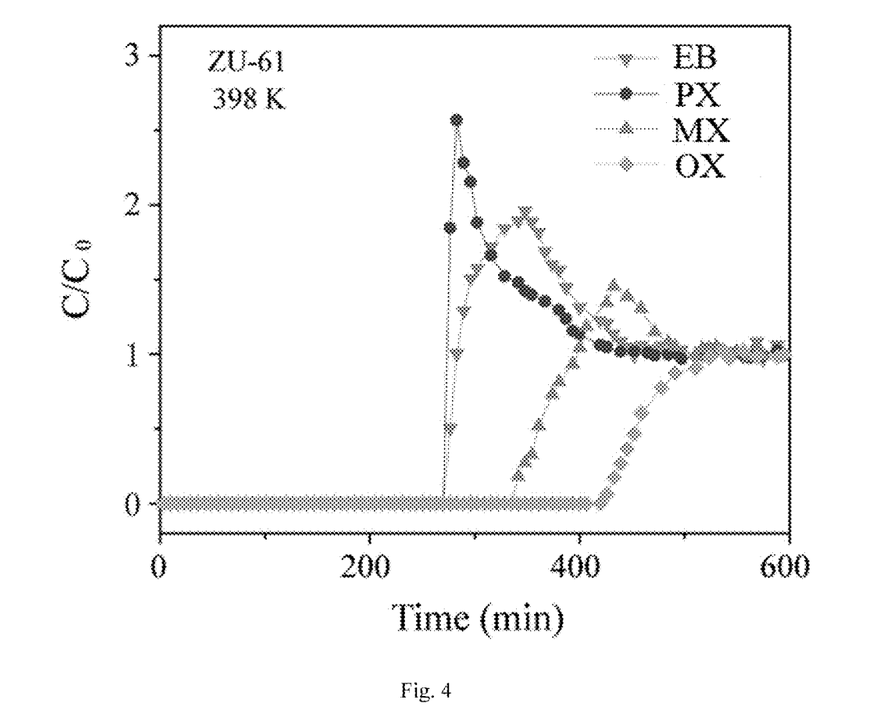
FIG. 4 shows the breakthrough curves obtained in the example 5.

The ZU-61 prepared in example 4 was loaded into a 50 mm long column, then the p-xylene, m-xylene, o-xylene and ethylbenzene (1/1/1/1, mass ratio) mixture obtained through nitrogen bubbling was introduced into the column at 20-40 mL/min with an operating temperature of 60° C., and high-purity p-xylene can be obtained from the effluent gas. The adsorbed column was purged by $N_2$ flow for 15 hours and then could be reused. The breakthrough curve shown in FIG. 4 demonstrates that this material can realize the separation of the above-mentioned C8-aromatics.

Example 6

Figure 5:
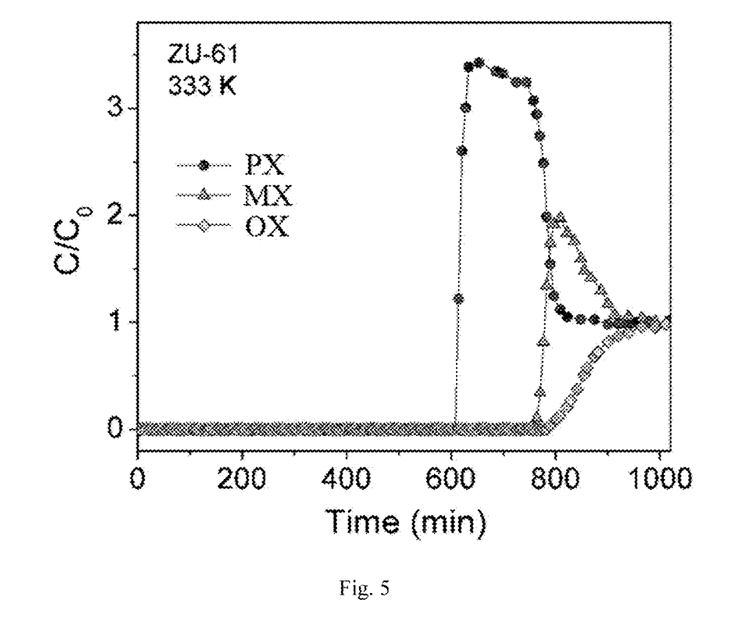
FIG. 5 shows the breakthrough curves obtained in the example 6.

The ternary p-xylene, m-xylene and o-xylene (1/1/1, mass ratio) gas mixture obtained through nitrogen bubbling was introduced into the column illustrated in the example 5 at 20-40 mL/min with an operating temperature of 60° C. As shown in FIG. 5, high-purity p-xylene (over 99.9%, mass percentage) can be obtained from the effluent gas.

Example 7

Figure 6:
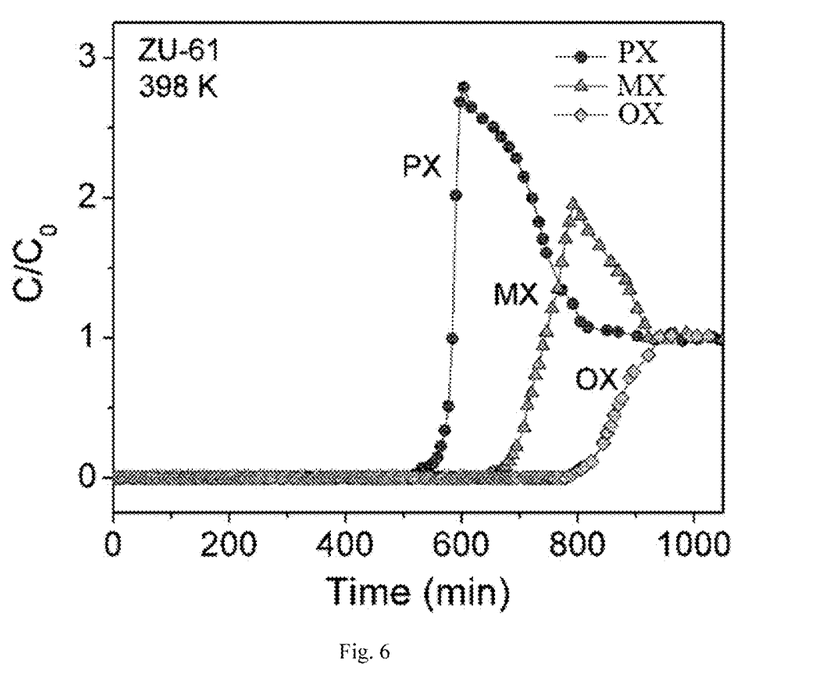
FIG. 6 shows the breakthrough curves obtained in the example 7.

The ternary p-xylene, m-xylene and o-xylene (1/1/1, mass ratio) gas mixture obtained through nitrogen bubbling was introduced into the column illustrated in the Example 5 at 20-40 mL/min with an operating temperature of 120° C. As shown in FIG. 6, high-purity p-xylene (over 99.9%, mass percentage) can be obtained from the effluent gas.

Example 8

Figure 7:
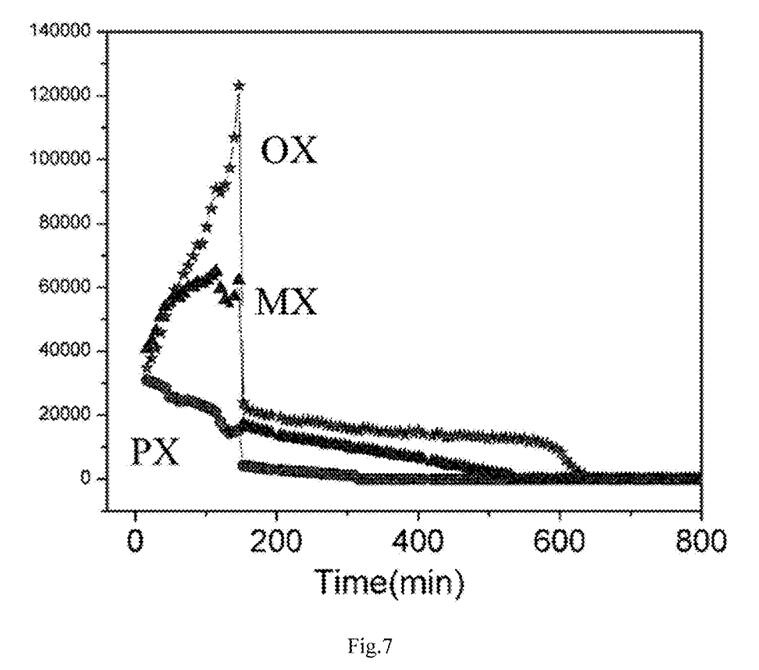
FIG. 7 shows the regeneration curves of the breakthrough experiments on adsorbent ZU-61 in the example 8.

The ternary p-xylene, m-xylene and o-xylene (1/1/1, mass ratio) gas mixture obtained through nitrogen bubbling was introduced into the column illustrated in the example 5 at 20-40 mL/min with an operating temperature of 120° C. High-purity p-xylene (over 99.9%, mass percentage) can be obtained from the effluent gas. The adsorbed column was purged by N₂ flow for 6-15 hours and then could be reused. The regeneration curves of sample are shown in FIG. 7.

Example 9

Figure 8:
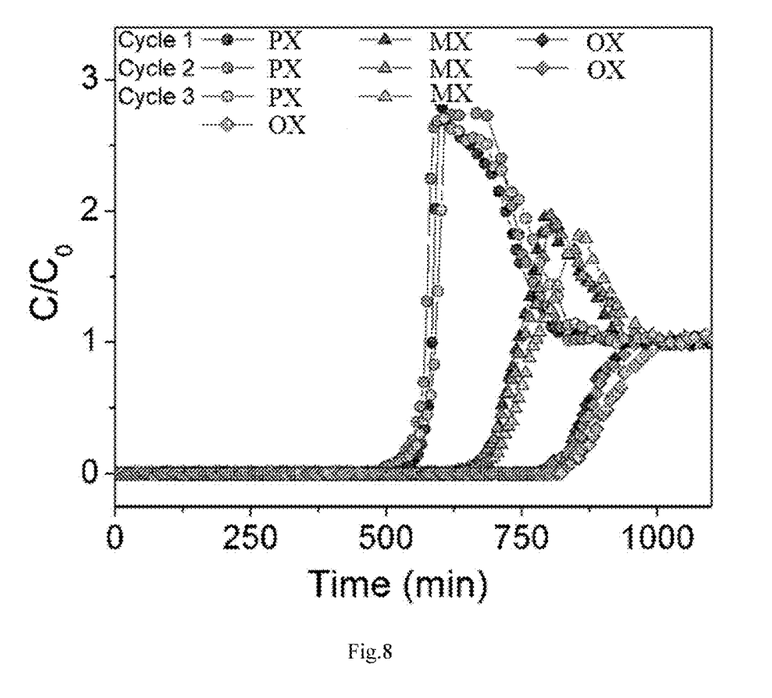
FIG. 8 shows the cycling breakthrough curves obtained in the example 9.
Figure 9:
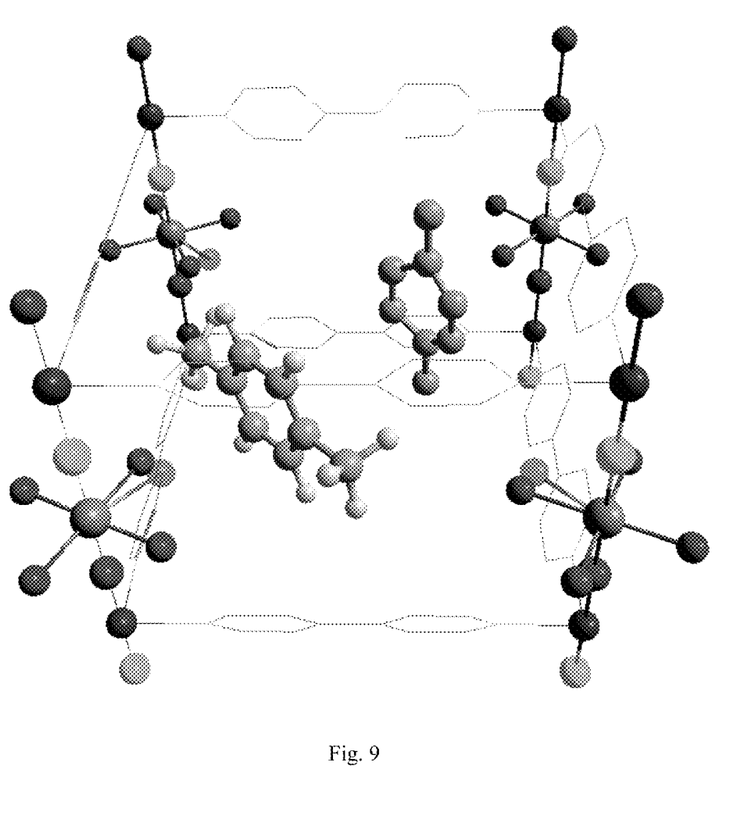
FIG. 9 shows the crystal structure diagram of the anion-pillared microporous material obtained in example 4 after adsorption of p-xylene.

The ternary p-xylene, m-xylene and o-xylene (1/1/1, mass ratio) gas mixture obtained through nitrogen bubbling was introduced into the column illustrated in the example 5 at 20-40 mL/min with an operating temperature of 120° C. High-purity p-xylene (over 99.9%, mass percentage) can be obtained from the effluent gas. The adsorbed column was purged by N₂ flow for 6-15 hours and then could be reused. The cycle curves of sample shown in FIG. 8 demonstrate the stability of the material.

Furthermore, the foregoing descriptions of the embodiments according to the present invention are provided for illustration only, not for the purpose of limiting the invention as defined by the appended claims and their equivalents. Although only the selected embodiments have been chosen to illustrate the present invention, the all involved change or modification without departing from the scope of the invention as defined in the appended claims are covered in this invention.

The invention claimed is:

1. A method for separating C8 aromatic hydrocarbon isomers, comprising the steps of using anion-pillared metal-organic framework materials as adsorbents, contacting the adsorbents with C8 aromatic hydrocarbon isomers, thus achieving selective adsorption and separation of a mixture of C8 aromatic hydrocarbon isomers;
wherein, the anion-pillared microporous materials are porous materials formed by metal ion M, inorganic anion A and organic ligand L through coordination bonds, with the general formula of [MAL₂]$_n$, where n>4 and n is an integer;
wherein the metal ion M is Fe²⁺, Co²⁺, Ni²⁺, Cu²⁺;
wherein the inorganic anion A is SiF₆²⁻, NbOF₅²⁻, TaF₇²⁻, ZrF₆²⁻, TiF₆²⁻, GeF₆²⁻, SO₃CF₃⁻, NbF₆⁻;
wherein the organic ligand L is selected from any of the following:

2. The method according to claim 1, wherein the pore size of the anion-pillared metal-organic framework materials disclosed herein is 5-10 Å.

3. The method according to claim 1, wherein the metal ion M is Ni²⁺ or Cu²⁺, the inorganic anion A is NbOF₅²⁻, SiF₆²⁻ or TiF₆²⁻, and the organic ligand L is 4,4'-bipyridine.

4. The method according to claim 1, wherein the mixture of C8 aromatic isomers is gaseous and/or liquid, which contains at least two of p-xylene, m-xylene, o-xylene and ethylbenzene.

5. The method according to claim 1, wherein the contact mode of the descried adsorbent and the C8 aromatic isomer mixture is any one of fixed-bed adsorption and simulated moving bed adsorption.

6. The method according to claim 5, wherein the adsorption temperature is 20-250° C., and the adsorption pressure is 0.1-5 bar.

7. The method according to claim 5, wherein the contact method is fixed-bed adsorption, which specifically comprises the following steps:
1) introducing the mixture of C8 aromatic isomers into a fixed-bed adsorption column, wherein strongly adsorbed C8 components are adsorbed on the adsorbent, and the specific C8 components that are not adsorbed or had low adsorption capacity are first penetrated to obtain the specific C8 components;
2) after the breakthrough and adsorption of the specific C8 components are completed, desorbing the strongly adsorbed C8 components from the adsorbent by means of decompression desorption, heating desorption, desorber desorption or inert gas purging to obtain them.

8. The method according to claim 7, wherein the desorption temperature is 20-250° C.

9. The method according to claim 7, wherein the described specific C8 component is p-xylene, and the mass percent purity is greater than 99.9%.

10. A method of selective adsorption and separation of C8 aromatic hydrocarbon isomers comprising the step of using anion-pillared microporous materials in contact with the C8 aromatic hydrocarbon isomers, wherein the anion-pillared microporous materials are porous materials formed by metal ion M, inorganic anion A and organic ligand L through coordination bonds, with the general formula of [MAL₂]$_n$, where n>4 and n is an integer;
wherein the metal ion M" is Fe²⁺, Co²⁺, Ni²⁺, Cu²⁺0;
wherein the inorganic anion A is SiF₆²⁻, NbOF₅²⁻, TaF₇²⁻, ZrF₆²⁻, TiF₆²⁻, GeF₆²⁻, SO₃CF₃⁻, NbF₆⁻;
wherein the organic ligand L is selected from any of the following:

* * * * *